United States Patent
Dahl et al.

(10) Patent No.: US 6,610,496 B1
(45) Date of Patent: Aug. 26, 2003

(54) PREDICTION OF GROWTH PERFORMANCE AND COMPOSITION IN ANIMALS, INCLUDING CATTLE, FROM RESPONSE TO GROWTH HORMONE RELEASING HORMONE

(75) Inventors: Geoffrey E. Dahl, Columbia, MD (US); Scott M. Barao, Woodbine, MD (US); Erin E. Connor, Elkridge, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 09/349,409

(22) Filed: Jul. 8, 1999

Related U.S. Application Data
(60) Provisional application No. 60/091,995, filed on Jul. 8, 1998.

(51) Int. Cl.⁷ ........................ G01N 33/53; G01N 33/543
(52) U.S. Cl. ................... 435/7.1; 435/4; 435/287.2; 435/810; 436/63; 436/164; 436/501; 436/518; 436/536; 436/811; 436/817; 424/130.1; 424/158.1; 424/520; 424/529; 424/530; 424/531; 530/399
(58) Field of Search ................ 424/130.1, 158.1, 424/520, 529, 530, 531; 435/7.1, 287.2, 810, 4; 436/164, 811, 817, 501, 536, 63, 518; 530/399

(56) References Cited

U.S. PATENT DOCUMENTS

| | | | | |
|---|---|---|---|---|
| 4,460,576 A | * | 7/1984 | Kawauchi | 424/177 |
| 4,585,756 A | * | 4/1986 | Brazeau, Jr. et al. | 514/12 |
| 4,833,166 A | * | 5/1989 | Grosvenor et al. | 514/12 |
| 4,839,344 A | * | 6/1989 | Bowers et al. | 514/16 |
| 4,880,778 A | * | 11/1989 | Bowers et al. | 514/12 |
| 5,061,690 A | * | 10/1991 | Kann et al. | 514/12 |
| 5,065,748 A | * | 11/1991 | Bercu | 128/630 |
| 5,317,017 A | * | 5/1994 | Ok et al. | 514/211 |
| 5,416,073 A | * | 5/1995 | Coy et al. | 514/12 |
| 5,428,013 A | * | 6/1995 | Mugica | 514/12 |
| 5,486,505 A | * | 1/1996 | Bowers et al. | 514/16 |
| 5,559,128 A | * | 9/1996 | Chakravarty et al. | 514/323 |
| 5,643,595 A | * | 7/1997 | Lewis | 424/422 |
| 5,691,377 A | * | 11/1997 | Estienne et al. | 426/656 |
| 5,721,250 A | * | 2/1998 | Morriello et al. | 514/318 |
| 5,721,251 A | * | 2/1998 | Chen et al. | 514/318 |
| 5,767,118 A | * | 6/1998 | Nargund et al. | 514/226.4 |
| 5,767,124 A | * | 6/1998 | Draper et al. | 514/278 |
| 5,811,074 A | * | 9/1998 | Bercu et al. | 424/9.1 |
| 5,962,416 A | * | 10/1999 | Buonomo | 514/12 |
| 6,013,622 A | * | 1/2000 | Bruno et al. | 514/2 |

FOREIGN PATENT DOCUMENTS

| | | | |
|---|---|---|---|
| EP | 0 289 186 A2 | * | 11/1988 |
| EP | 0 363 063 A2 | * | 4/1990 |
| EP | 0 413 839 A1 | * | 2/1991 |
| WO | WO 94/11396 | * | 5/1994 |

OTHER PUBLICATIONS van der Walt, J.G. Somatotropin Physiology—a review. Journal of Animal Science (1994) vol. 24, No. 1, pp. 1–9.*

Moellers et al. Pulsatile Infusion of growth hormone–releasing factor depresses growth of young broiler chickens. Comp. Biocem. Physiol. (1994) vol. 107A, No. 4, pp. 665–672.*

Dubreuil et al. Effect of Porcine Growth Hormone–Releasing Factor (1–29) NH2 and Thyrotropin–Releasing Factor on Pig Growth Performance. Can. J. Anim. Sci. (1990) vol. 70, pp. 459–467.*

McAndrews et al. Age–related changes in the secretion of growth hormone in vivo and in vitro in infantile and pre-pubertal Holstein bull calves. Journal of Endocrinology. (1993) vol. 139, pp. 307–315.*

Zinn et al. Growth hormone response after administration of growth hormone–releasing factor to proven dairy sires. Livestock Production Science. vol. 40 (1994) pp. 157–164.*

Lovendahl et al. The effect of genetic selection for milk yield on the response to growth hormone secretagogues in immature cattle. J. Endocrinology. vol. 128 (1991) pp. 419–424.*

Connor et al. Predicting bull performance from growth hormone response to growth hormone–releasing hormone. J. Anim. Sci. vol. 75, No. Supp. 1 (1997) pp. 170.*

Suttie et al. Genetically lean and fat sheep differ in their growth hormone response to frowth hormone–releasing factor. Domestic Anim. Endocrin. vol. 8, No. 2 (1991) pp. 323–329.*

Woolliams et al. Endogenous pulsing and stimulated release of growth hormone in dairy calves of high and low genetic merit. Anim. Prod. vol. 56 (1993) pp. 1–8.*

* cited by examiner

*Primary Examiner*—Long V. Le
*Assistant Examiner*—Kartic Padmanabhan

(57) ABSTRACT

A method for predicting animal growth performance, which includes administering a suitable amount of growth hormone releasing hormone (GHRH) to an animal, observing levels of growth hormone (GH) subsequent to GHRH administration and; predicting growth and fat development in an the animal from observed levels of GH.

15 Claims, 4 Drawing Sheets

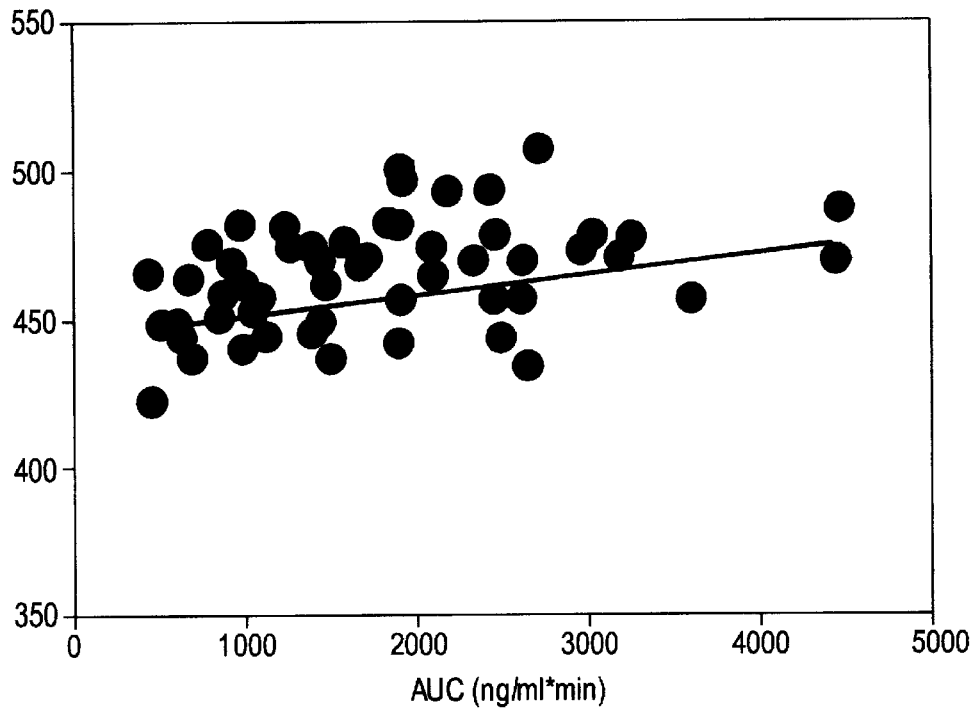

FIG. 1 Significant positive relationship (P=.003) between area under the GH response curve (AUC-GH) and bodyweight (BW) at d140 in Angus bulls during a 140-d "bull test." Weights were adjusted to initial mean BW. Bulls (n=56) were injected with 1.5ug GHRH/100kg BW.

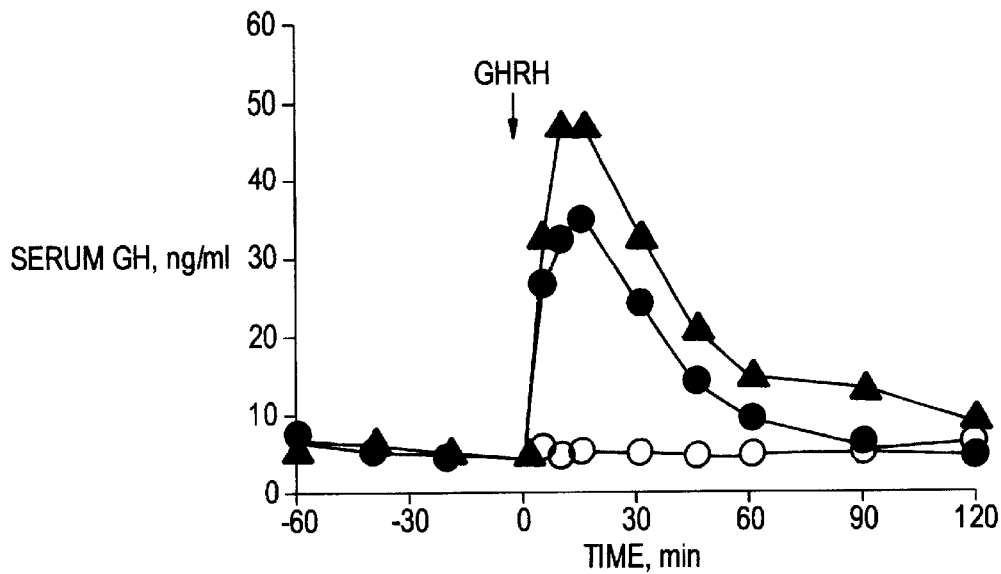

FIG. 3 Mean GH responses in weaning Angus bulls (n=56) to three intravenous injections of GHRH (SEM=1.87); 0 μg/100 kg BW (O), 1.5 μg/100 kg BW (O), and 4.5 μg/100 kg BW (Δ). The three doses of GHRH were administered to bulls in a Latin square design balanced for residual effects.

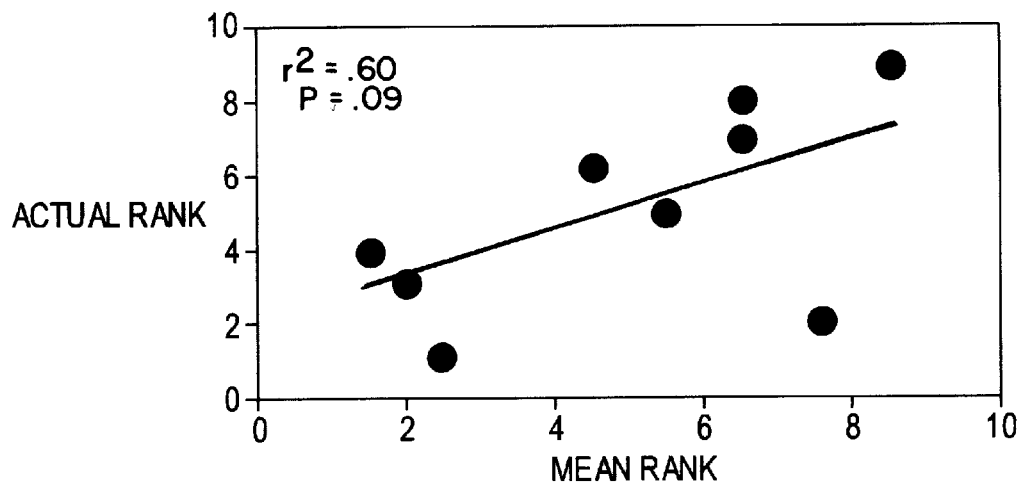

FIG. 2A Ranks of responses of a subsample of bulls (n=9) to two injections of GHRH (1.5 ug/100 Kg BW) 7 days apart, and to BW rank at d 112 of test. Each bulls mean area under the GH response curve (AUC-GH) rank versus that animals BW rank at d 112 of "bull test."

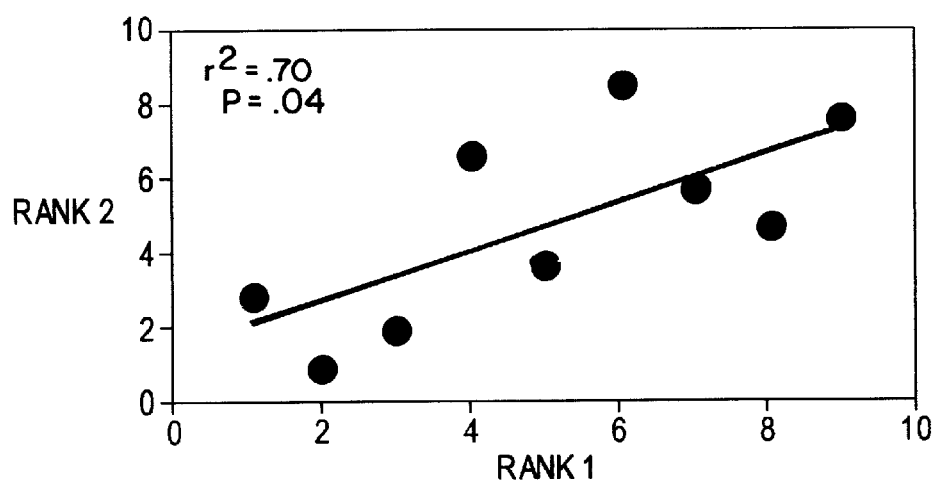

FIG. 2B Ranks of responses of a subsample of bulls (n=9) to two injections of GHRH (1.5 ug/100 Kg BW) 7 days apart, and to BW rank at d 112 of test. Rank of each bulls response to GHRH on sample d1 (rank 1) vs. sample day 2 (rank 2) 7 days later.

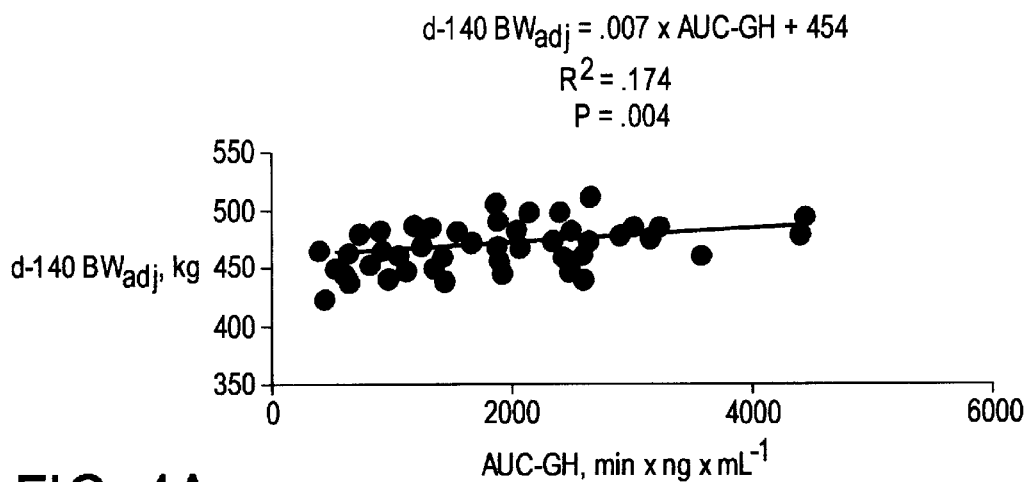

FIG. 4A

The relationships in Angus bulls (n=56) between adjusted body weight on d 140 of the growth performance test (d-140 $BW_{adj}$, kg) versus GH response to intravenous GHRH injection as determined by area under the GH response curve (AUC-GH, min x ng x $mL^{-1}$); 1.5 μg GHRH/100 kg BW

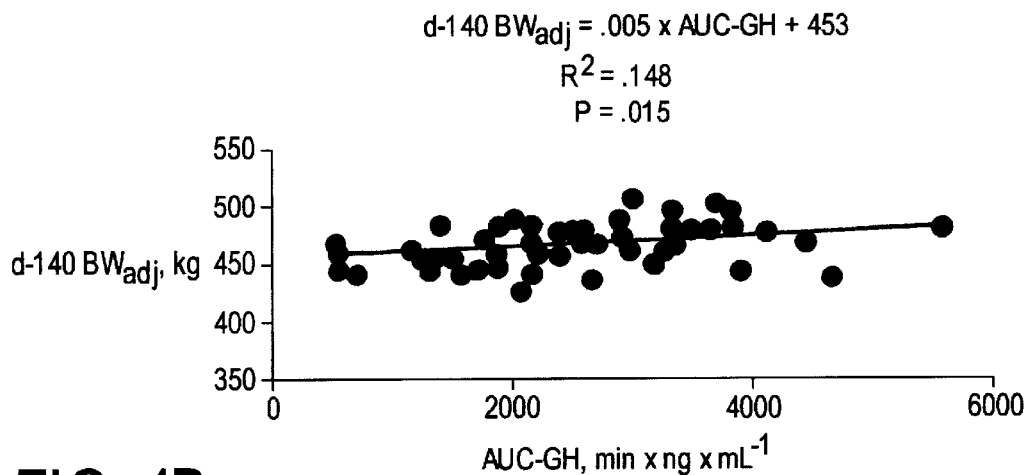

FIG. 4B

The relationships in Angus bulls (n=56) between adjusted body weight on d 140 of the growth performance test (d-140 $BW_{adj}$, kg) versus GH response to intravenous GHRH injection as determined by area under the GH response curve (AUC-GH, min x ng x $mL^{-1}$); 4.5 μg GHRH/100 kg BW The relationship in Angus bulls (n=56) between ADG (kg/d) versus GH response to intravenous injection of 1.5 μg GHRH/100 kg BW as determined by area under the GH response curve (AUC-GH, min x ng x mL$^{-1}$)

PREDICTION OF GROWTH PERFORMANCE AND COMPOSITION IN ANIMALS, INCLUDING CATTLE, FROM RESPONSE TO GROWTH HORMONE RELEASING HORMONE

CONTINUING APPLICATION INFORMATION

This application claims priority from Provisional Application Serial No. 60/091,995, filed Jul. 8, 1998, which application is incorporated herein by reference in its entirely.

FIELD OF THE INVENTION

The present invention relates to a method for predicting animal growth performance, which includes administering a suitable amount of growth hormone releasing hormone (GHRH) to an animal, observing levels of growth hormone (GH) subsequent to GHRH administration and; predicting growth and fat development in an the animal from observed levels of GH. The invention also relates to a test kit for practicing the method of the invention.

BACKGROUND OF THE INVENTION

Beef currently accounts for 58% of all red meat consumed in the United States, constituting over $50 billion in retail value (1). Thus, beef production is a major contributor to the agricultural economy of the U.S., and its sustained and improved competitiveness is imperative. There is increasing consumer demand for leaner beef due to concerns over saturated fat consumption (2). Also excess fat accumulation on carcasses represents wasted resources of producers and cost to the packer. Producers, therefore, are interested in methods to decrease the fat content of beef while maintaining and improving the rate of gain. These two goals can at times be in conflict.

A path to improvement in both areas is to enhance the ability to select bulls of superior genetic potential for rapid, lean gain. Because over 90% of the beef cattle in the U.S. are bred by natural service, such a selection procedure would involve a large number of animals. Indeed, there are approximately 11,000 bulls selected each year on an official "bull test" at a cost of $300 to $400 per bull (3). A simple, accurate method to select bulls early in life for rapid, lean gain has tremendous potential to save producers money, increase the rate of genetic improvement, and provide consumers with a healthier product.

It is a common practice to select animals based on growth performance. The process is conducted under controlled feeding conditions. Limitations to this approach include the duration of time to obtain usable results, limited information on composition of gain, and the expense per animal.

Recently, interest has focused on identification of "growth" genes and their use in Marker Assisted Selection schemes. Indeed, a number of polymorphisms have been identified in genes of the bovine somatotrophic axis, including growth hormone (GH) (5–7), GH-receptor (8,9), and GH-releasing hormone (GHRH; 10). The impact of these polymorphisms on growth, however, has been less well defined. That is, little association has been made between specific sequence variations and subsequent physiologic responses and compositional data.

In contrast to genetic data, there is considerable information available attempting to correlate physiologic variables, such as spontaneous GH release with production and carcass endpoints (11–18). However, there has been considerable inconsistency in the utility of unstimulated GH as a selection criterion. Thus, recent efforts in dairy cattle have focused on the use of responses to GHRH, a specific stimulator of GH release and synthesis (19–21). Such an approach decreases variability associated with environmental factors and represents a more accurate index of an animal's ability to secrete GH than an acute, unstimulated sample. It is well established that GH is intimately involved in the process of growth and lean mass accretion in particular. Indeed, hypophysectomy of rats and other animals leads to a reduction in growth (26). Total reversal of this effect of hypophysectomy occurs only when GH is replaced (26). In cattle, immunological hypophysectomy via active immunization against GHRH results in marked reductions in circulating GH and IGF-1 as well as smaller, fatter animals (32,33). There is slight or no correlation between growth and mean concentrations of GH in cattle (12). Klindt et al. (11) found no correlation between characteristics of pulsatile GH release and growth in lambs. In contrast, in lambs that were selected for fat or lean carcass composition, lean lambs exhibited differences in pulsatile GH release and tended to have higher mean circulating GH concentrations (18). It is quite possible that external factors that affect GH secretion varied among these experiments, and such variability masked any true differences. Nevertheless, it appears that basing selection decisions on spontaneous GH would be of limited value.

In contrast to growth, there is a significant relationship between spontaneous GH secretion and milk production in cattle. Higher circulating GH is observed in dairy cows selected for superior milk production (15,17), and certain aspects of pulsatile GH release were observed to be positively correlated with genetic potential in dairy bulls (14). Disadvantages, such as environmental factors, remain a limitation to application of GH quantification in selection for genetic merit.

The hypothalamic hormone growth hormone-releasing hormone (GHRH) stimulates anterior pituitary gland secretion of GH, which increases lipolysis and, via IGF-1, promotes protein synthesis and growth of long bones. Exogenous GH increases rate of gain and decreases carcass fat percentage in cattle (Groenewegen et al., 1990; Binelli et al., 1995) and lambs (McLaughlin et al., 1994) and increases milk yield in dairy cows (Bauman et al., 1985). Administration of GHRH to lambs improves growth rate and lean gain (Beerman et al., 1990) and increases milk production in dairy cows (Dahl et al., 1991, 1993).

Problems and environmental influences are exacerbated in beef production systems because the range of environmental conditions that animals are exposed to is greater due to the quantity of animals maintained for natural service.

In an attempt to minimize environmental influences on selection, a robust method developed in dairy bulls associates GrH responses to GHRH with estimates of genetic potential. There is a significant, positive correlation of MFP$ (economic index for milk traits) of a bull with the area under the GH response curve (AUC-GH) upon GHRH challenge (19,20). Similarly, sheep selected for fatness over lean have a lower AUC-GH than those selected for lean gain (34).

Accretion of body mass, i.e. growth, is essential to the production of red meat. GH in turn, is critical to normal animal growth. In addition, GH is necessary for normal lactation in ruminants. For these reasons a great deal of research has focused on understanding GH secretion and actions, and has led to the use of exogenous GH, or its secretagogue GHRH, to enhance the efficiency of animal production. Elevation of circulating GH can markedly reduce fat accretion which increases the desirability of meat products by an increasingly health conscious public.

An understanding of the central nervous control of GH secretion as provided by the present invention results in new methods to select for animals superior in endogenous GH secretion, and therefore increase the production efficiency and consumer acceptability of animal products. Because of its role in ruminant growth and lactation, variation in GH secretion may provide a tool to assess an animals potential for meat or milk production. Secretion patterns of GH including peak frequency and peak duration are related to dairy merit; however, mean serum GH is not related to dairy merit (Klindt, 1988; Kazmer et al., 1990, 1991). Purchas et al. (1970) found no relationship between basal GH and growth performance of cattle and no relationship has been demonstrated between GH pulse characteristics and growth of lambs (Klindt et al., 1985) nor cattle (Ohlson et al., 1981). Conversely, sheep and cattle selected for rapid gain exhibit higher plasma GH concentrations than unselected lines (Dodson et al., 1983; Ohlson et al., 1987).

In contrast, pituitary gland responsiveness to GHRH is a reliable indicator of dairy merit and provides more consistent results than spontaneous serum GH measurement (Lovendahl et al., 1991; Zinn et al, 1994). Further, studies of fat and lean sheep (Suttie et al., 1991) suggest that responsiveness to GHRH is predictive of composition of gain. The objective of the present study was to determine whether GH response to a GHRH challenge in young beef bulls is predictive of subsequent growth performance and carcass traits.

Thus, the capacity for GH release is of critical importance to growth in cattle. Increasing the knowledge of the control of GH release would lead to new methods of controlling growth in cattle, particularly with regard to reducing fat accumulation. In addition, such knowledge would enhance the ability to select breeding animals that transmit superior traits for growth. Despite the requirement of GH for normal growth, attempts to correlate circulating levels with performance in individuals has yielded inconsistent results.

The present invention overcomes deficiencies in prior art methods of predicting growth performance in animals, particularly beef cattle.

SUMMARY OF THE INVENTION

An object of the present invention is to provide a method for predicting animal growth performance, comprising increasing circulating levels of GHRH in an animal; observing levels of GH subsequent to GHRH increases and; predicting growth of the animal from observed levels of GH.

In another embodiment the invention provides a method for predicting animal growth performance, comprising administering a suitable amount of growth hormone releasing hormone (GHRH) to an animal, observing levels of growth hormone (GH) subsequent to GHRH administration, and predicting growth of the animal from observed levels of GH.

Advantageously, the invention provides a method for predicting animal fat, comprising administering a suitable amount of growth hormone releasing hormone (GHRH) to an animal, observing levels of growth hormone (GH) subsequent to GHRH increases and; predicting animal fat gain from observed levels of GH.

In an additional embodiment the invention provides a test kit for testing animal growth performance, comprising, (A) a suitable amount of growth hormone releasing hormone, (B) a container for collection of blood sample, (C) an antibody for detection of GH, and (D) a means for detecting said antibody.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF THE DRAWINGS

FIG. 1 shows a significant positive relationship (P=0.003) between area under the GH response curve (AUC-GH) and bodyweight (BW) at d140 in Angus bulls during a 140-d "bull test". Weights were adjusted to initial mean BW. Bulls (n=56) were injected with 1.5 $\mu$g GHRH/100 kg BW.

FIG. 2 shows ranks of responses of a subsample of bulls (n=9) to two injections of GHRH 1.5 $\mu$g (GHRH/100 kg BW) 7 days apart, and to BW rank at d112 of test. Panel A. Each bulls mean area under the GH response curve (AUC-GH) rank versus that animals BW rank at d112 of "bull test". Panel B. Rank of each bulls response to GHRH on sample d1 (rank) versus sample d2 (rank2) 7 days later.

FIG. 3 shows injection of GHRH caused a rapid increase in circulating GH in nearly all bulls tested with peak GH concentration occurring on average within 15 min of GHRH injection. AUC-GH averaged across all animals within treatment exhibited a dose dependent response to GHRH (P<0.001).

FIG. 4 shows the relationships between d-140 $BW_{adj}$ versus AUC-GH for the 1.5 and 4.5 $\mu$g/100 kg BW dose of GHRH were similar.

DETAILED DESCRIPTION OF THE INVENTION

Figure 5:
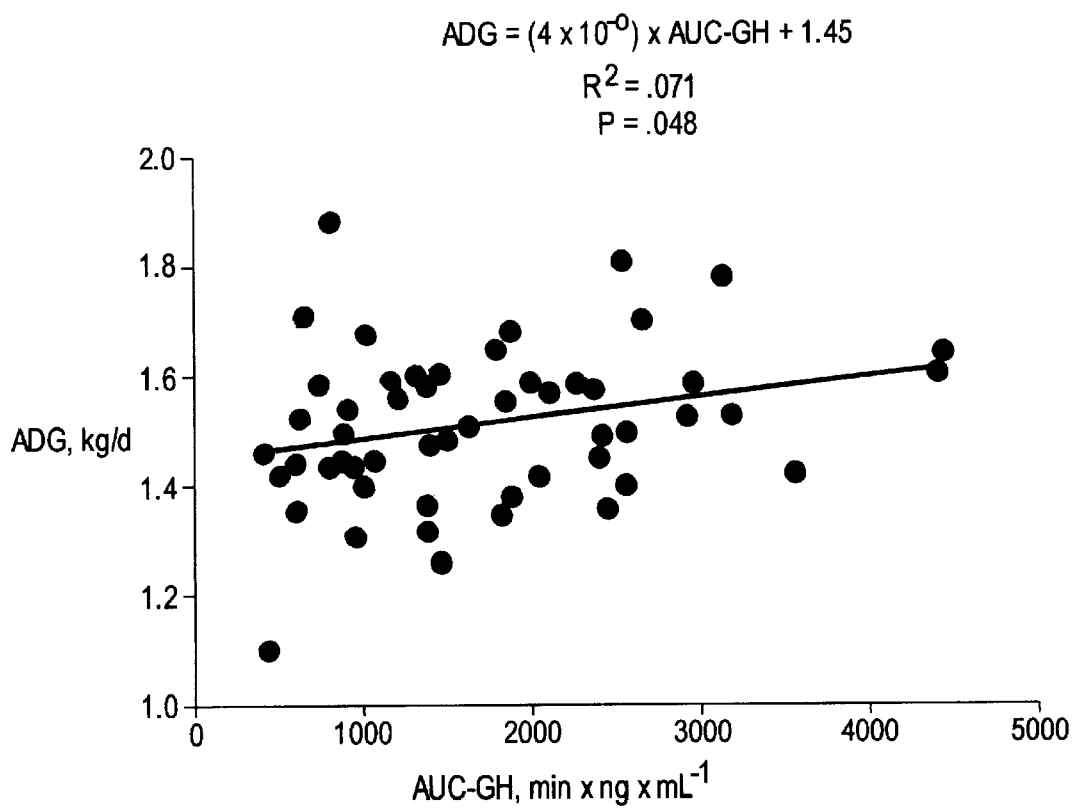
FIG. 5 shows only GH response to 1.5 Ag HRH/100 kg BW was predictive of ADG.

The present invention is directed to a method for predicting animal growth performance, comprising administering a suitable amount of growth hormone releasing hormone (GHRH) to an animal, observing levels of growth hormone (GH) subsequent to GHRH administration, and predicting growth of the animal from observed levels of GH. The levels of growth hormone are observed in blood. In a preferred embodiment the levels of growth hormone are observed in blood serum.

In accordance with the present invention a suitable amount of growth hormone releasing hormone administered may be about 1 to about 25 $\mu$g/100 kg BW of animal. In a preferred embodiment the amount of growth hormone releasing hormone administered may be about 1.5 to about 5.0 $\mu$g/100 kg BW of animal. In the present method the level of growth hormone is preferably observed from about 10 to about 15 minutes after administration of GHRH, as this period is generally the peak response time of GH to GHRH.

In accordance with the present invention the animal may be any commercial animal which is consumed for its meat and preferably, may be a cow. The animal is preferably a dairy cow or beef cow. In one embodiment the cow is a heifer or a bull. In an alternative embodiment the cow is selected from the breed of holstein, roan, Angus, Hereford, charlois, etc.

The invention similarly provides a method for predicting animal fat, comprising administering a suitable amount of growth hormone releasing hormone (GHRH) to an animal, observing levels of growth hormone (GH) subsequent to GHRH increases and; predicting animal fat from observed levels of GH.

In order to practice the methods of the present invention the invention provides for a test kit for testing animal growth performance, comprising, (A) a suitable amount of growth hormone releasing hormone, (B) a container for collection of blood sample, (C) optionally, an antibody for detection of GH, and (D) a means for detecting said antibody. A syringe or other blood collection device may be included in the kit. In a preferred embodiment the antibody is a monoclonal antibody. In a preferred embodiment the antibody is that which has been designated Accession Number FE-R-1-1-4, publically available from the USDA Hormone and Pituitary Program, Building 200, United States Department of Agriculture, Agricultural Research Service, Beltsville, Md. 20705.

Throughout the present specification where compositions, kits, and methods are described as including or comprising specific components, it is contemplated by the inventors that compositions of the present invention also consist essentially of or consist of the recited components.

The following examples further describe the present invention.

EXAMPLE 1

GHRH Challenge

The potential for predicting bull growth performance characteristics from GH response to GHRH (35) was evaluated. Fifty-six Angus bulls averaging 228 d of age received three intra venous doses (0, 1.5 and 4.5 $\mu$g/100 kg BW) of human GHRH (obtained from Hoffman LaRoche) (1–29) analog in a randomized block design and evaluated for GH response. AUC-GH exhibited a significant ($P<0.001$) GHRH dose response. Regression analysis was used to study the relationship between AUC-GH and body weight gain from a 140-d bull test (FIG. 1). At both doses, a significant positive ($P<0.05$) relationship between AUC-GH and change in BW was observed. In addition, there was a significant negative ($P<0.05$) relationship between carcass fat and AUC-GH. Thus, GH response to GHRH in young bulls is associated with subsequent growth characteristics and may be a useful sire selection criterion in beef production.

Realizing however, that transfer of the technique to the producer level requires a simpler sampling scheme, a second study was conducted to determine if a single point sample following GHRH injection would be predictive of subsequent growth and carcass composition. Results from the earlier study showed that the peak of the GH response occurred between 10 and 15 minutes following GHRH challenge. Based on that data, 54 bulls were sampled 10 minutes after a challenge with GHRH (obtained from Pharmacia UpJohn). The results show a strong relationship between AUC-GH and BW at d112 ($P<0.01$).

A random subsample of bulls from this study were used to estimate the within animal repeatability of the single injection technique. One week following the first challenge, the bulls (n=9) received a second GHRH challenge (1.5 $\mu$g/100 kg BW). The rank correlation of AUC-GH1 with that of AUC-GH2 was significant ($P<0.05$; FIG. 2). Further, the rank of AUC-GH was directly related to the growth response at d112 ($P<0.09$). Thus these data indicate the technique is repeated repeatable and predictive.

EXAMPLE 2

The following example includes revised data from Example 1.

GHRH Challenge

Fifty-six (56) weanling Angus bulls (Wye cross). Bulls averaged 229 d (SD=27) of age and 239 kg. BW (SD=34). Bulls were maintained in four groups of approximately 15 animals each in covered loose housing under natural photo period Bulls were provided ad libitum access to feed consisting of corn silage, shelled corn and protein supplement to provide a gain of 1.3 kg/d according to NRC requirements (NRC, 1996). Bulls were offered feed once daily between 0700 and 0800. Feed was last offered to bulls at least 12 h before GH challenge. Pedigree data from which direct weanling weight EPD (WWEPD) values were calculated were available for only 55 of the bulls tested. All experimental procedures were performed according to animal use regulations.

The GHRH challenge was conducted in mid-September. All bulls were catheterized 1 d prior to GH challenge and blood collection. Catheters were flushed with 100 U sodium heparin (Elkins-Sinn, Inc., Cherry Hill, N.J.) in 0.9% saline to prevent blood clot formation. Bulls received three doses (0, 1.5 and 4.5 $\mu$g/100 kg BW) of human GHRH (1–29) analog (Hoffmann-LaRoche Ro23-7863, Nutley, N.J.). One dose of GHRH was administered to each bull during each of three consecutive 3-h blood collection periods in a Latin square design balanced for residual effects. The GHRH was diluted to a final concentration of 5 $\mu$g/mL in 0.9% saline with 0.1% bovine serum albumin (Sigma, St. Louis, Mo.) and injected to achieve the desired doses of 1.5 and 4.s $\mu$g/100 kg BW. All bulls were restrained by halter in a corral during blood sampling and GH injection. Blood (5 mL) was collected via a jugular catheter (Abocath 14 Ga×5.5 in LA Indwelling Radiopaque i.v. Catheter-Teflon, 4535-84) at −60, −45, −30, −15, 0, 5, 10, 15, 30, 45, 60, 90 and 120 min relative to GHRH injection. On the first day of treatment, 27 bulls were challenged with GHRH (15 bulls beginning at 1000 and 12 bulls beginning at 1300) and on the 2nd day, 29 bulls were treated (14 bulls at 1000 and 15 bulls at 1130). Blood samples were stored at room temperature for 2 to 4 h and then at 4° C. for a maximum of 72 h. Serum was harvested from whole blood after centrifugation (1850 g, 20 min, 4° C.) and stored at −20° C. until assayed for GH. Serum GH concentration was measured by RIA using the method of Elsasser et al. (1989). Bovine serum (25 to 200) depressed binding in parallel to the standard curve in the GH assay and spike recovery averaged 110%. Mean inter- and intrassay coefficients of variation (15 assays) were 7.90 and 3.29%, respectively; assay sensitivity averaged 0.89 ng/mL. Concentration of GH was plotted over time and total GH response was determined by calculating the area under the response curve (AUC-GH) by trapezoid summation. One week following the GHRH challenge experiment, all bulls were evaluated by a 140 d growth performance test during which BW, hip height (%DHH) and scrotal circumference were measured every 28 d. Ultrasound was performed on d 140 of the growth performance test to estimate external backfat thickness (EBF), ribeye area (REA and percentage intramuscular fat (IMF). All animals were scanned with an Aloka 500V real-time diagnostic ultrasound unit (Aloka USA, Wallingford, Conn.) equipped with a 172 scanning width, 3.5-MHz linear array transducer (UST-5049-3.5) using a technique similar to that of Perkins et al. (1992). To determine the accuracy of the ultrasound estimates, 13 of the bulls were slaughtered 4 d after ultrasound to obtain actual measurements of EBF and REA.

Results showed a relationship between AUC from the 1.5 µg/100 kg BW does and %BW at day 28 (P=0.03), day 56 (P=0.02), day 84 (P=0.07) and day 112 (p=0.06). The relationship between AUC and %DHH was significant (P=0.02) at day 28 of the bull test, but not at day 56, day 84 or day 112. Thus growth hormone response to GHRH in young bulls is associated with subsequent growth and is useful in sire selection criterion in beef production.

Statistical Analyses

All statistical analyses were conducted using the SAS System v. 612 (SAS Institute Inc., 1989 to 1996). AUC-GH in response to the three doses of GHRH (0, 1.5, and 4.5 µg/100 kg BW was analyzed by ANOVA to determine if a GHRH dose response existed. Linear regression was used to adjust BW data for differences in weaning weight (WW). The adjustment equation was $Y_{adj}=Y_{observed} \times b$ ($X_{Observed}$ − mean of X), where Y is BW at d-140 of the growth performance test (d-140 $BW_{adj}$), X is WW, and b is the least squares linear regression coefficient for Y regressed on X. Linear regression was used to evaluate the following relationships: 1) the ability to predict d-140 $BW_{adj}$, on-test ADG and carcass ultrasound measurements from AUC-GH, 2) the relationships between weaning weight adjusted to 205 d of age (205-d WW) versus on-test and carcass ultrasound measurements; and 3) the relationships between WWEPD versus on-test ADG and carcass ultrasound measurements. For models including AUC-GH as the independent predictor variable, a mixed model procedure was used with collection time (block) as a random effect. To compare ultrasound estimates of EBF and REA to actual measurements collected at slaughter from a subset of 13 bulls, the differences between actual measurements and ultrasound estimates for each animal were calculated and plotted against actual measurements.

Bulls exhibited projected feed consumption and growth, gaining an average of 1.5 kg/d during the 140 day growth performance test period.

AUC-GH Predicts day-140 $BW_{adj}$ and ADG

Injection of GHRH caused a rapid increase in circulating GH in nearly all bulls tested with peak GH concentration occurring on average within 15 min of GHRH injection (FIG. 3). Indeed, AUC-GH averaged across all animals within treatment exhibited a dose dependent response to GHRH (P<0.001, FIG. 3). Two bulls, however, exhibited practically no increase in serum GH concentration in response to both 1.5 and 4.5 µg GHRH 100 kg BW. Responses to GHRH in both animals were below 640 min×ng×mL$^{-1}$ versus an overall mean saline response (n=56) of 657 min×ng×mL$^{-1}$. Because no technical limitation was noted during the injections, their data were included in the analyses. The relationships between d-140 $BW_{adj}$ versus AUC-GH for the 1.5 and 4.5 µg/100 kg BW dose of GHRH were similar (FIG. 4; Table 1). Only GH response to 1.5 µg GHRH/100 kg BW was predictive of ADG (FIG. 5). Neither WWEPD nor 205-d WW were predictive of ADG (Table 1).

Ultrasound Accurately Estimates Carcass Measurements

Measurements of actual carcass EBF and REA of a subset of 13 bulls collected at slaughter were consistent with ultrasound estimates. Mean (1 SE) EBF estimated by ultrasound was 0.81 (±0.05) cm versus actual EBF which averaged 0.81 (±0.08) cm. Ultrasound estimated mean REA at 78.42 (±2.66) cm$^2$ and actual averaged 74.64 (±1.92) cm$^2$. A plot of actual carcass measurements versus the calculated differences between actual measurements and ultrasound estimates showed that ultrasound estimates of REA and EBF were consistent with actual measurements on an individual animal basis.

AUC-GH Predicts Carcass Fat; 205-d WW and WWEPD Predict REA

In general, estimates of carcass fat (i.e., EBF and IMF) decreased with increasing AUC-GH values; although, the strength of the relationships between AUC-GH and carcass characteristics varied, depending on the dose of GHRH administered (Table I). There was no relationship between REA and AUC-GH in response to either 1.5 or 4.5 µg GHRH/100 kg BW. Both 205-d WW and WWEPD were directly related to REA but neither predicted measurements of carcass fat (Table 1).

As observed in similar studies in Holsteins (Kazmer et al., 1992; Zinn et al., 1994) injection of human GHRH (1–29) analog in the present study increased serum GH concentration of weanling beef bulls in a dose-responsive manner. We demonstrated that injection of as little as 1.5 µg GH/100 kg BW results in a robust increase in serum GH. Results of studies relating dairy merit to GH response to GHRH (Kazmer et al., 1992; Zinn et al., 1994) revealed that doses in excess of 22 µg GHRH/100 kg BW are less effective in identifying superior dairy sires than concentrations between 4 and 11 µg GHRH/100 kg BW. Indeed, previous studies support the concept that differences in milk production traits are related more to pituitary gland sensitivity rather than maximal response to GHRH (Zinn et al., 1994). In the present study, GH response to both the 1.5 and 4.5 µg/100 leg BW doses of GHRH were predictive of bull growth performance. To our knowledge, this study is the first to demonstrate a relationship between GH response to GHRH and future growth characteristics of young, unproven beef bulls.

The physiologic mechanism underlying high GH responders versus low GH responders to the same dose of GHRH is not known Pituitary gland sensitive to GHRH may play a significant role. Increases in pituitary sensitivity to GH among animals may be due to increased GHRH receptor number, increased binding affinity of GH receptor for GHRH, or increased efficiency of post-receptor signal transduction. Further research in these areas could be useful for identifying animals with greater growth potential and desirable carcass characteristics.

A number of studies investigating the GH axis and its relationship with growth performance characteristics focus on IGF-1. Both positive and negative associations between rates of gain in cattle and serum IGF-1 concentration have been reported (LundLarsen, 1977; Davis and Simmen, 1997; Stick et al., 1998). For example, Anderson et al. (1988) observed a negative correlation between mean serum IGF-1 concentration versus carcass fat and a positive correlation between IGF-1 versus carcass protein. The ability to select for high or low serum IGF-1 concentration has been demonstrated (Davis and Bishop, 1991; Enns et al., 1991, Davis and Simmen, 1997) and the usefulness of its selection in animal production is clearly evident. However, a number of environmental factors influence secretion of IGF-1 in cattle including photo period (Dahl et al., 1997) and nutritional status (McGuire et al., 1992). Due to the variability associated with IGF-1 release, its measured association with growth characteristics is limited. Furthermore, the presence of GH binding proteins and difficulty in their measurement compounds the problems related to measuring available IGF-1 affecting growth. In any case, the relationships between IGF-1 and growth or carcass characteristics examined thus far have been associative rather than predictive of growth potential. The use of a stimulated release of GH to assess an animal's growth potential and carcass characteristics is less likely to be influenced by environmental factors, should therefore be less variable, and should provide a more consistent relationship with growth. Because GHRH integrates the various influences on GH secretion, we believe that GHRH challenge is a more reliable physiological indicator of growth and composition of gain than IGF-1.

Because EPDs and WW may be used by producers as selection criteria, as compared the use of WWEPD and 205-d WW to GH response to GHRH as indicators of subsequent growth performance and carcass traits. Although WWEPD refers to predicted performance of a sire's offspring and not the individual sire, we believe that WWEPD may be informative of a sire's future performance because he must possess the trait of interest in order to transmit it to his offspring. No relationships were found between WWEPD versus weight gain nor carcass fat, yet WWEPD was associated with REA, a characteristic not predicted by GH response to GHRH. Likewise, 205-d WW was related to REA but not ADG nor ultrasound estimates of carcass fat. Therefore, GH response to GHRH provides useful information that WWEPD and 205-d WW do not provide and could be combined with WWEPD and 205-d WW to select the most desirable sires. Also, whether WWEPD values of sires are related to the GHRH responsiveness of their offspring can be explored. Planned matings of high and low GH-responding bulls are made in an effort to develop high and low GHRH responsive lines to address this question.

The present invention shows a positive relationship was found between GH response to GHRH and weight gain and an inverse relationship was found between GH response and body to fat measurements. Animals with a greater sensitivity to GHRH to have a greater propensity to secrete GH, resulting in greater lean mass accretion and less fat deposition than animals with a lesser sensitivity to GHRH. Specific relationships between carcass fat measurements and GH response to GHRH were not consistent between the two doses of GHRH administered but the general tendency of an inverse relationship between GH response and carcass fat held true. Because carcass ultrasound measurements were conducted at d 140 of the growth performance test, carcass finishing was incomplete and ultrasound measurements likely were not representative of each bull's true finishing potential. Actual carcass evaluation of a subset of 13 bulls indicated that ultrasound estimates of carcass composition at d 140 of the growth performance test were accurate. A consistent relationship between GH response and carcass fat measurements is verified when carcass evaluation is conducted at a later stage of growth.

Results of the present study indicate that in young, growing beef bulls, growth hormone response to injection of growth hormone-releasing hormone is predictive of future growth performance and carcass composition. In the present invention, growth hormone response was a better predictor of composition of future gain than 205-d weaning weight or weaning weight EBF values.

EXAMPLE 3

Responsiveness to Growth Hormone Releasing Hormone (GH) Challenge: A Physiological Indicator of Average Daily Gain in Beef Bulls The relationship between serum growth hormone (GH) concentration after GHRH-stimulated release, and subsequent weight gain in weanling black Angus bulls (n=38) was evaluated. Bulls averaged 272 d (SD=29) of age when challenged with 1.5 and 4.5 $\mu$g/100 kg BW bovine GHRH (1–30) analog (i.v.) following a 19-h fasting period. All bulls were challenged with one of 2 doses of GHRH on consecutive days and dose was randomized by day. Two hours prior to each GHRH challenge, all bulls received a "clearance" dose of 4.5 $\mu$g/100 kg BW bovine GHRH (1–30) analog to reduce variation in subsequent response to GHRH challenge. Blood was collected via jugular venipuncture at 0 and 10 min relative to each injection of GHRH for serum GH determination by RIA. Pearson's ranked correlation revealed responses from the two 4.5 $\mu$g GHRH/100 kg BW clearance doses were consistent within animal over time (®=0.38; P=0.03). The relationships between GH response to each challenge dose of GHRH versus ADG during a 112-d growth performance test were evaluated using simple linear regression. A positive relationship (®=0.18; P=0.007) was demonstrated between GH response to the 1.5 $\mu$g GHRH/100 kg BW challenge versus ADG. Response to the 4.5 $\mu$g GHRH/100 kg BW challenge tended to be positively related to subsequent weight gain ($r^2$=0.08; P=0.09). The relationship between response to GHRH challenge and carcass composition at d 112 of the growth performance test are evaluated. Results of this study show that GH response to GHRH challenge is a useful tool for identifying beef bulls superior for growth.

EXAMPLE 4

Use of Growth Hormone (GH) Response to Growth Hormone-Releasing Hormone (GHRH) to Determine Growth Potential in Beef Heifers A test was performed to determine whether the GH response to a challenge dose of GHRH is predictive of rapid, lean growth in the beef heifer. GH response to a challenge of GHRH was measured in 67 Angus heifers averaging 225 d (SD=21) of age. Blood samples were taken immediately prior to and 10 min following a clearance dose of 4.5 $\mu$g GHRH/100 kg BW (injected i.v.) and, 2 hr later, immediately prior to and 10 mil following a challenge dose of either 1.5 or 4.5 $\mu$g GHRH/100 kg BW. The GHRH was a bovine analog (1–30) GHRH (Pharmacia Upjohn). Each animal received both challenge doses, which were randomly assigned across the 2 d of blood collection. Concentrations of GH in serum were measured by RIA. BW was measured every 28 d, and ADG was calculated at the end of a 140 d growth test. The clearance dose stabilized the within animal variation of response to the challenge doses (P<0.0001). There was a dose response to the two GHRH challenges (P<0.05). A positive relationship (®=0.52, P<0.0001) was found between the heifers" rankings for each dose, i.e. high responders to the low dose were high responders to the high dose. The correlation between ADG and predicted ADG was 0.21 (P<0.07) for a model based on treatment (1.5 $\mu$g GHRH/100 kg BW). For heifers (n=28) whose sires (n=3, Hl; n=2, LO) were selected for their GH response to GHRH, the correlation was 0.47 (P<0.01) for a model including the effect of sire and treatment (both doses). As with Angus bulls, the results show that GH response to an injection of GHRH may be used as a predictor of growth in beef heifers. It is also believed that there is a relationship between carcass composition and maternal ability (e.g. milk production) of beef heifers and their GH response to GHRH challenge.

TABLE 1

Regression coefficients of growth and carcass measurements of Angus bulls (n = 56) regressed on GH response to intravenous GHRH injection, 205-d weaning weight (205-d WW) and direct weaning weight EPD (WWEPD)

| Response Variable | Statistic | AUC-GH1.5[a] | AUC-GH4.5[b] | 205-d WW | WWEPD |
|---|---|---|---|---|---|
| ADG[c] | Slope (SE) | $4 \times 10^{-5}$ ($2 \times 10^{-5}$)* | $1 \times 10^{-5}$ ($2 \times 10^{-5}$) | .001 (.001) | .003 (.004) |
|  | SD | .14 | .14 | .14 | .14 |
|  | $R^2$ | .07 | .01 | .05 | .01 |
| REA[d] | Slope (SE) | $8 \times 10^{-4}$ ($1.2 \times 10^{-3}$) | $5 \times 10^{-4}$ (.001) | .14 (.04)** | .50 (.21)* |
|  | SD | 8.50 | 8.51 | 7.78 | 8.17 |
|  | $R^2$ | .01 | .00 | .17 | .09 |
| IMF[e] | Slope (SE) | $-7 \times 10^{-5}$ ($2 \times 10^{-4}$) | $-5 \times 10^{-4}$ ($2 \times 10^{-4}$)* | .001 (.01) | -.002 (.05) |
|  | SD | 1.74 | 1.66 | 1.74 | 1.76 |
|  | $R^2$ | .00 | .09 | .00 | .00 |
| EBF[f] | Slope (SE) | $-7 \times 10^{-5}$ ($2 \times 10^{-5}$)** | $8 \times 10^{-6}$ ($2 \times 10^{-5}$) | $4 \times 10^{-4}$ (.001) | -.006 (.005) |
|  | SD | .17 | .19 | .19 | .19 |
|  | $R^2$ | .12 | .00 | .00 | .02 |

[a]GH response to 1.5 μg GHRH/100 kg BW.
[b]GH response to 4.5 μg GHRH/100 kg BW.
[c]Average daily gain, kg/d.
[d]Ribeye area, cm$^2$.
[e]Intramuscular fat, %.
[f]External backfat, cm.
*P < .05.
**P < .01.
***P < .001

REFERENCES

The following references are herein incorporated by reference:

1. U.S. Poultry and Red Meat Consumption, Prices, Spreads, and Margins 1993 USDA Economic Research Service, National Agricultural Statistics Service Stock #AIB-684.
2. Barkema A, Drabenstott M, Welch K 1991 The quiet revolution in the U.S. food market. Economic Review May/June pp. 25–41
3. Beef Improvement Federation Proceedings 1996 Ron Bolze, ed. Colby, K S
4. Hallerman E M, Nave A, Kashi Y, Holzer Z, Soller M, Beckmann J S 1987 Restriction fragment length polymorphisms in dairy and beef cattle at the growth hormone and prolactin loci. Anim Genet 18:213–222
5. Cowan C M, Dentine M R, Ax R L, Schuler L A 1989 Restriction fragment length polymorphisms associated with growth hormone and prolactin genes in Holstein bulls: evidence for a novel growth hormone allele. Anim Genet 20:157
6. Lucy M C, Hauser S D, Eppard P J, Krivi G G, Collier R J 1991 Genetic polymorphism within the bovine somatotropin (bST) gene detected by polymerase chain reaction and endonuclease digestion. J Dairy Sci 74 (Suppl 1):284
7. Unanian M M, DeNise S K, Zhang H M, Ax R L 1994 Rapid communication: polymerase chain reaction-restriction fragment length polymorphism in the bovine growth hormone gene. J Anim Sci 72:2203
8. Sneyers M, Renaville R, Devolder A, Massart S, Burny A, Portetelle D 1992 Variability in the bovine GH receptor amino acid sequence. J Endocrinol Invest 15 (Suppl. 4), Abstract No. 5954
9. Falaki M, Gengler N, Sheyers M, Prandi A, Massart S, Formigoni A, Burny A, Portetelle D, Renaville R 1996 Relationships of polymorphisms for growth hormone and growth hormone receptor genes with milk production traits for Italian Holstein-Friesian bulls. J Dairy Sci 79:1446–1453
10. Moody D E, Pomp D, Barendse W 1995 Rapid communication: restriction fragment length polymorphism in amplification products of the bovine growth hormone-releasing hormone gene. J Anim Sci 73:3789
11. Klindt J, Jenkins T G, Leymaster K A 1985 Relationships between some estimates of growth hormone and prolactin secretion and rates of accretion of constituents of body gain in rams. Anim Prod 41:103–111
12. Purchas R W, Macmillan K L, Hafs H D 1970 Pituitary and plasma growth hormone levels in bulls from birth to one year of age. J Anim Sci 31:358–363
13. Davis M E, Bishop M D 1991 Preliminary results on between and within twin set variation in insulin-like growth factor I (IGF- 1) and some relationships with performance traits in 24 identical twin heifers. Livest Prod Sci 27:255–262
14. Kazmer G W, Canfield R W, Bean B 1990 Plasma somatotropin and prolactin concentrations in young dairy sires before and after a 24-hour fast. J Dairy Sci 73:3112–3117
15. Kazmer G W, Barnes M A, Akers R M, Pearson R E 1986 Effect of genetic selection for milk yield and increased milking frequency on plasma growth hormone and prolactin concentration in holstein cows. J Anim Sci 63:1220–1227
16. Robinson D L, Hammond K, Graser H-U, McDowell G H 1992 Relationships between breeding values and physiological responses to fasting and refeeding in dairy bulls. J Anim Breed Genet 109:26–36
17. Barnes M A, Kazmer G W, Akers R M, Pearson R E 1985 Influence of selection for milk yield on endogenous hormones and metabolites in holstein heifers and cows. J Anim Sci 60:271–284
18. Suttie J M, Veenvliet B A, Littlejohn R P, Gluckman P D, Corson I D, Fennessy P F 1993 Growth hormone pulsatility in ram lambs of genotypes selected for fatness or leanness. Anim Prod 57:119–125
19. Lovendahl P, Angus K D, Woolliams J A 1991 The effect of genetic selection for milk yield on the response to growth hormone secretagogues in immature cattle. J Endocrinol 128:419–424

20. Zinn S A, Kazmer G W, Rycroft H, Campbell R M 1994 Growth hormone response after administration of growth hormone-releasing factor to proven dairy sires. Livest Prod Sci 40:157–164
21. Kazmer G W, Zinn S A 1996 Serum growth hormone concentrations after administration of various dosages of growth hormone-releasing factor and somatostatin in Holstein heifer calves. J Anim Sci 74(Suppl 1):100 (Abstract)
22. Frohman L A, Jansson J O 1986 Growth hormone-releasing hormone. Endocrine Rev 7:223–253
23. Millard W J 1989 Central regulation of growth hormone secretion. Animal Growth regulation, pp 237–255. Campion, D R Housman G J, Martin R I eds. Plenum Publ. NY, N.Y.
24. Plotsky P M, Vale W 1985 Patterns of growth hormone-releasing factor and somatostatin secretion into the hypophysial-portal circulation of the rat. Science 230:461–463
25. Wehrenberg W B, Guistina A 1992 Basic counterpoint: mechanisms and pathways of gonadal steroid modulation of growth hormone secretion. Endocrine Rev 13:799–308
26. Davis S L 1988 Recent concepts in regulation of growth by GH and IGF J Anim Sci 66 (Suppl. 3):84–97
27. Harvey S, Scanes C G, Daughaday W H 1995 Growth Hormone. CRC Press, Boca Raton Fla.
28. McCusker R H, Clemmons D R 1992 The insulin-like growth factor binding proteins: structure and biological functions. In The Insulin-like Growth Factors. 1st edition Schofield P N, ed Oxford Univ Press, Oxford UK
29. Sato M, Frohman L A 1993 Differential effects of central and peripheral administration of growth hormone (GH) and insulin-like growth factor on hypothalamic GH-releasing hormone and somatostatin gene expression in GH-deficient dwarf rats. Endocrinology 133:793–799
30. Carro E, Senaris R, Considine R V, Casanueva F F, Dieguez C 1997 Regulation of in vivo growth hormone secretion by leptin. Endocrinology 138:2203–2206
31. Qunitela M, Senaris R, Heiman M L, Casanueva F F, Dieguez C 1997 Leptin inhibits in vitro hypothalamic somatostatin secretion and somatostatin mRNA levels. Endocrinology 138:5641–5644
32. Trout W E, Schanbacher B D 1990 Growth hormone and insulin-like factor-I responses in steers actively immunized against somatostatin or growth hormone-releasing factor. Endocrinology 125:123–129
33. Simpson R B, Armstrong J D, Harvey R W, Miller D C, Heimer E P, Campbell R M 1991 Effect of active immunization against growth hormone-releasing factor on growth and onset of puberty in beef heifers. J Anim Sci 69:4914–4924
34. Suttie J M, Lord E A, Gluckman P D, Fennessy P F Littlejohn R P 1991 Genetically lean and fat sheep differ in their growth hormone response to growth hormone-releasing factor. Domest Anim Endo 8(2):323
35. Connor E E, Barao S M, Douglass L W, Dahl G E 1997 Predicting bull performance from growth hormone response to growth hormone-releasing hormone. J. Anim. Sci. 75(Suppl. 1):170. Abstract#138
36. Connor E E, Barao S M, Russek-Cohen E, Dahl G E 1998 Evaluation of a simple blood test to predict growth performance of beef bulls. J. Anim. Sci. 76 (Suppl. 1): Submitted
37. Frohman L A, Downs T R, Clarke I J, Thomas G B 1990 Measurement of growth hormone releasing hormone and somatostatin in hypothalamic-portal plasma of unanesthetized sheep. J Clin Invest 86:17–24
38. Thomas, B G, Cummins J T, Francis H, Sudbury A W, Mcloud P I, Clarke I J 1991 Effect of restricted feeding on the relationship between hypophysial portal concentrations of growth hormone (GH)-releasing factor and somatostatin, and jugular concentrations of GH in ovariectomized ewes. Endocrinology 128:1151–1158
39. Varner, M A, Davis S L, Reeves J J 1980 Temporal serum concentrations of growth hormone, thyrotropin, insulin, and glucagon in sheep immunized against somatostatin. Endocrinology 106:1027–1032
40. Spencer G S G, Garssen G J, Hart I C 1983 A novel approach to growth promotion using auto-immunization against somatostatin. I. Effects on growth and hormone levels in lambs. Livest Prod Sci 13:142–152
41. Vicini J L, Clark J H, Hurley W L, Bahr J M 1988 The effect of immunization against somatostatin on growth and concentration of somatotropin in plasma of holstein calves. Domest Anim Endo 5:35–45
42. Chomczynski P, Sacchi N 1987 Single-step method of RNA isolation by acid guanidinium thiocyanate-phenol-chloroform extraction. Analytical Biochem 162:156–159
43. Davies C J, Andersson L, Joosten I, Mariani P, Gasbarre L C, Hensen E J 1992 Characterization of bovine MHC class II polymorphism using three typing methods:serology, RFLP and IEF. Eur J Immunogenet 19 (5):253–62
44. Hankins O G, Howe P E 1946 Estimation of the composition of beef carcasses and cuts. USDA Tech Bull No 926, Washington DC
45. Rohan R M, Rexroad C E Jr, Guthrie H D 1991 Changes in the concentration of mRNAs for the inhibin subunits in ovarian follicles after the administration of gonadotropins to progestin treated ewes. Dom Anim Endo 8:445–454
46. Fourney R M, Miyakoshi J, Day R S III, Paterson M C 1988 Northern blotting: Efficient RNA staining and transfer. Focus 10:5–7
47. Elsasser T H, Rumsey T S, Hammond A C 1989 Influence of diet on basal and growth hormone-stimulated plasma concentrations of IGF-1 in beef cattle. J Anim Sci 67:128–141
48. Weaver R F, Weissman C 1979 Mapping of RNA by modification of the Berk-Sharp procedure: The 5' termini of 15S β-globin MRNA and mature 10S β-globin mRNA have identical map coordinates. Nucl Acids Res 7:1175–1193
49. Gaylinn B D, Harrison J K, Zysk J R, Lyons C E, Lynch K R, Thorner M O 1993 Molecular cloning and expression of a human anterior pituitary receptor for growth hormone-releasing hormone. Mol Endocrinol 7:77–84
50. Takahashi T, Okimura Y, Yoshimura K, Shigeyoshi Y, Kaji H, Abe H, Chihara K 1995 Regional distribution of growth hormone-releasing hormone (GHRH) receptor mRNA in the rat brain. Endocrinology 136:4721–4724
51. Gaylinn B D, von Kap-Herr C, Golden W L, Thorner M O 1994 Assignment of the human growth hormone-releasing hormone receptor gene (GHRHR) to 7p14 by in situ hybridization. Genomics 19:193–195
52. Solinas-Toldo S, Lengauer C, Fries R 1995 Comparative genome map of human and cattle. Genomics 27:489–496
53. Shepard A R, Zhang W, Eberhart N L 1994 Two CGTCA motifs and a GHFl/Pitl binding site mediate cAMP-dependent protein kinase A regulation of human growth hormone gene expression in rat anterior pituitary GC cells. J Biol Chem 269:1804–1814
54. Smith K P, Liu B, Scott C, Sharp D Z 1995 Pit-1 exhibits a unique promoter spacing requirement for activation and synergism. J Biol Chem 270:4484–4491
55. Benoist C, O'Hare K, Breathnach R. Chambon P 1980 The ovalbumin gene-sequence of putative control regions. Nucl Acids Res 8:127–142

56. Grosveld G C, Rosenthal A, Flavell R A 1982 Sequence requirements for the transcription of the rabbit-globin gene in vivo: the 80 region. Nucl Acids Res 10:4951–4971
57. Anderson, P. T., W. G. Bergen, R. A. Merkel, W. J. Enright, S. A. Zinn, K. R. Refsal, and D. R. Hawkins. 1988. The relationship between composition of gain and circulating hormones in growing beef bulls fed three dietary crude protein levels. J. Anim. Sci. 66:3059–3067.
58. Bauman, D. E., P. J. Eppard, M. J. DeGeeter, and G. M. Lanza 1985. Responses of high producing dairy cows to long-term treatment with pituitary somatotropin and recombinant somatotropin. J. Dairy Sci. 68:1352–1362.
59. Beermann, D. H., D. E. Hogue, V. K Fishell, S. Aronica, H. W. Dickson, and B. R. Schriker. 1990. Exogenous human growth hormone releasing factor and ovine somatotropin improve growth performance and composition of gain in lambs. J. Anim. Sci. 68:4122–4133.
60. Binelli, M., W. K. Vanderkooi, L. T. Chap, M. J. Vandehaar, J. D. Turner, W. M. Moseley, and H. A. Tucker. 1995. Comparison of growth hormone-releasing factor and somatotropin—body growth and lactation of primiparous cows. J. Dairy Sci. 78:2129–2139
61. Dahl, G. E., L. T. Chapin, M. S. Allen, W. M. Moseley, and H. A. Tucker. 1991. Comparison of somatotropin and growth hormone-releasing factor on milk yield, serum hormones, and energy status. J. Dairy Sci. 74:3421–3428
62. Dahl, G. E., L. T. Chapin, W. M. Moseley, and H. A. Tucker. 1993. Galactopoietic effects of recombinant somatotropin and growth hormone-releasing factor in dairy cows. J. Dairy Sci. 76:1550–1557.
63. Dahl, G. E., T H Elsasser, A. V. Capuco, R. A. Erdman, and R. R. Peters. 1997. Effects of a long day photoperiod on milk yield and circulating concentrations of insulin-like growth factor-I. J. Dairy Sci. 80:2784–2789
64. Davis, M. E., and R. C. .M. Simmen 1997. Genetic parameter estimates for serum insulin-like growth factor I concentration and performance traits in Angus beef cattle. J. Anim. Sci, 75:317–324.
65. Dodson, M. V., S. L. Davis, D. L. Ohlson, and S. K. Ercanbrack. 1983, Temporal patterns of growth hormone, prolactin and thyrotropin secretion in targhee rams selected for rate and efficiency of gain. J. Anim. Sci. 57:338–342.
66. Enns, R M, J. S. Brinks, K. Hossner, and R. G. Mortimer. 1991. Parameter estimates of insulin-like growth factor I (IGF-I) and performance traits in beef cattle. J. Anim. Sci. 69 (Suppl. 1).204.
67. Groenewegen, P. P., B. W. McBride, J. H. Burton, and T. H, Elsasser. 1990. Effect of bovine somatotropin on the growth rate, hormone profiles and carcass composition of Holstein bull calves. Domest. Anim. Endocrinol. 7:43–54
68. Kazmer, G. W., R. W. Canfield, and B. Bean. 1991. Somatotropin and prolactin profile characteristics in proven AI dairy sires. J. Anim. Sci. 69:1601–1606.
69. Kazmer, G. W., S. A. Zinn, H Rycroft, and R. M Campbell 1992. Serum growth hormone in and semen characteristics of proven AI dairy sires after administration of growth hormone-releasing factor. Can. 1. Anim. Sci. 72:959–963.
70. Klindt, J. 1988. Relationships among growth hormone and prolactin secretory parameter estimates in Holstein bulls and their predicted differences for lactational traits J. Anim. Sci. 66:278:2790.
71. Lund-Larsen, T. R., A. Sundby, V. Kruse, and W. Velle. 1977. Relation between growth rate, serum somatomedin and plasma testosterone in young bulls. J. Anim. Sci. 44:189–194.
72. McGuire, M. A., J. L. Vicini, D. E. Bauman, and J. J. Veenhuizen. 1992. Insulin-like growth factors and binding proteins in ruminants and their nutritional regulation. J. Anim. Sct. 70:2901–2910
73. McLaughlin, C. L., H. B. Hendrick, I. J. Veenhuizen, R. L. Hintz, L. Munyakazi, T. R. Kasser, and C. A. Baile. 1994. Performance, clinical-chemistry, and carcass responses of finishing lambs to formulated Sometribove (methionyl bovine somatotropin). J. Anim. Sci. 72:2544–2551.
74. National Research Council. 1996. Nutrient Requirements of Beef Cattle, Seventh Edition. Washington, D.C., National Academy Press.
75. Ohlson, D L, R M Koch, J. Klindt, and S. L. Davis. 1987. Relations hip of growth hormone, prolactin and thyrotropin secretion to individual and progeny performance of hereford bulls. J. Anim. Sci. 65:63–67.
76. Ohlson, D. L., S. L. Davis, C. L. Ferrell, and T. G. Jenkins. 1981. Plasma growth hormone, prolactin and thyrotropin secretory patterns in hereford and simmental calves. J. Anim. Sci. 53:371–375.
77. Perkins, T, L., R. D. Green, K. E. Hamlin, H. H Shepard, and M. F. Miller. 1992. Ultrasonic prediction of carcass merit in beef cattle: Evaluation of technician effects on ultrasonic estimates of carcass fat thickness and longissimus muscle area. J. Anim. Sci. 70:2758–2765.
78. SAS Institute Inc. 1989–1996. Cary, N. C., USA.
79. Stick, D A, M. E. Davis, S. C. Loerch, and R C M Simmen. 1998. Relationship between blood serum insulin-like growth factor I concentration and postweaning feed efficiency of crossbred cattle at three levels of dietary intake. J. Anim Sci. 76:498–505.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

What is claimed is:

1. A method for predicting a relative future growth performance of individual animals in a random, unselected set of ruminant meat-producing animals of the same species, the method comprising the steps of:

providing a random, unselected set of ruminant meat-producing animals of the same species, and, for each animal, administering growth hormone releasing hormone (GHRH) to the animal so that a circulating level of GHRH in the animal is increased, observing levels of growth hormone (GH) subsequent to GHRH increases, comparing the GH levels of each animal to that of the other animals of the set of animals and predicting the relative future growth performance of each animal, wherein a higher relative level of GH in comparison to that of other animals of the set of animals indicates that an animal will have a greater relative lean mass accretion and a lesser relative fat deposition in comparison to other animals of the set of animals.

2. The method of claim 1, wherein the levels of growth hormone are observed in blood.

3. The method of claim 2, wherein the levels of growth hormone are observed in blood serum.

4. The method of claim 1 wherein the level of growth hormone is observed from about 10 to about 15 minutes after administration of GHRH.

5. The method of claim 1 wherein the animals are cattle.

6. The method of claim 5, wherein the cattle are selected from dairy cattle and beef cattle.

7. The method of claim 5, wherein the cattle are heifers or bulls.

8. The method of claim 5, wherein the cattle are selected from the group consisting of Holstein, Angus, Charolais, Hereford, and Roan.

9. A method for predicting a relative propensity of a random, unselected ruminant meat-producing animal to accumulate carcass fat, the method comprising the steps of providing a random, unselected ruminant meat-producing animal, administering an amount of growth hormone releasing hormone (GHRH) to the animal, observing levels of growth hormone (GH) subsequent to the administration of the growth hormone releasing hormone, comparing the observed levels of growth hormone with that of other random, unselected animals of the same species that have also been administered the same amount of growth hormone, and predicting the relative propensity of the animal to accumulate carcass fat in comparison to the propensity of the other random, unselected animals of the same species, a lower relative level of GH in comparison to the level of GH of the other animals indicating a greater relative propensity to accumulate carcass fat in comparison to the propensity of the other animals.

10. A method for predicting relative future growth performance of individual bovine animals in a random, uinselected set of bovine animals, the method comprising the steps of:

providing a random, unselected set of bovine animals, and, for each animal, administering growth hormone releasing hormone (GHRH) to the animal so that a circulating level of GHRH in the animal is increased, observing levels of growth hormone (GH) subsequent to GHRH increases, comparing the observed GH levels of each animal to that of other animals of the set of animals and predicting the relative future growth performance of each animal, wherein a higher relative level of GH in comparison to that of other animals of the set of animals indicates that an animal will have a greater relative lean mass accretion and a lesser relative fat deposition in comparison to other animals of the set of animals.

11. The method of claim 10, wherein the levels of growth hormone are observed in blood or blood serum.

12. The method of claim 10, wherein the level of growth hormone for each animal is observed from about 10 to about 15 minutes after administration of GHRH to the animal.

13. A method for predicting a relative propensity of a random unselected bovine animal to accumulate carcass fat, the method comprising the steps of:

administering an amount of growth hormone releasing hormone (GHRH) to a random, unselected bovine animal so that a circulating level of GHRH in the animal is increased;

observing levels of growth hormone (GH) subsequent to the adminition of the growth hormone releasing hormone, comparing the observed levels of growth hormone with that of other random, unselected bovine animals that have been administered the same amount of growth hormone releasing hormone and predicting the relative propensity of the animal to accumulate carcass fat in comparison to the propensity of the other animals, a lower relative level of GH in comparison to the level of GH of the other animals indicating a greater relative propensity to accumulate carcass fat in tissue in comparison to te propensity of the other animals.

14. The method of claim 13 wherein the level of growth hormone for each animal is observed in blood or blood serum taken from the animal from about 10 to about 15 minutes after administration of GHRH to the animal.

15. A method for predicting growth performance of a bovine animal relative to other bovine animals of the same sex comprising the steps of:

administering an amount of growth hormone releasing hormone to a bovine animal so that circulating levels of growth hormone releasing factor in the animal is increased;

observing levels of growth hormone (GH) subsequent to the administration of the growth hormone releasing hormone in the animal, comparing the observed levels of growth hormone in the animal with that of other bovine animals of the same sex that have been administered the some amount of growth hormone releasing hormone and predicting growth performance of the animals; the bovine animals with higher levels of GH relative to animals with lower levels of GH are predicted to have a better growth performance.

* * * * *